United States Patent
Barbagli et al.

(10) Patent No.: US 11,382,695 B2
(45) Date of Patent: Jul. 12, 2022

(54) SYSTEMS AND METHODS FOR INTELLIGENTLY SEEDING REGISTRATION

(71) Applicant: INTUITIVE SURGICAL OPERATIONS, INC., Sunnyvale, CA (US)

(72) Inventors: Federico Barbagli, San Francisco, CA (US); Timothy D. Soper, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 396 days.

(21) Appl. No.: 16/491,244

(22) PCT Filed: Mar. 22, 2018

(86) PCT No.: PCT/US2018/023791
§ 371 (c)(1),
(2) Date: Sep. 5, 2019

(87) PCT Pub. No.: WO2018/175737
PCT Pub. Date: Sep. 27, 2018

(65) Prior Publication Data
US 2020/0008874 A1    Jan. 9, 2020

Related U.S. Application Data

(60) Provisional application No. 62/474,866, filed on Mar. 22, 2017.

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 34/35* (2016.02); *A61B 90/37* (2016.02);
(Continued)

(58) Field of Classification Search
CPC ....... G06T 3/0068; A61B 34/20; A61B 34/35; A61B 34/10; A61B 90/37;
(Continued)

(56) References Cited

U.S. PATENT DOCUMENTS 6,331,191 B1   12/2001   Chobotov
6,380,732 B1   4/2002    Gilboa
(Continued)

FOREIGN PATENT DOCUMENTS

EP      2942029 A1       11/2015
WO      WO-2010093153 A2  8/2010
(Continued)

OTHER PUBLICATIONS

International Search Report and Written Opinion for Application No. PCT/US2018/023791, dated Jul. 20, 2018, 16 pages.
(Continued)

*Primary Examiner* — Brenda C Bernardi
(74) *Attorney, Agent, or Firm* — Haynes and Boone, LLP

(57) ABSTRACT

A medical system comprises a robotic manipulator arm and an imaging probe coupled to the robotic manipulator arm such that the imaging probe is movable in connection with the robotic manipulator arm. The system also comprises a control system in communication with the robotic manipulator arm and the imaging probe. The control system performs operations comprising extracting system information. The system information includes kinematic information from a robotic arm of a medical system, setup information, or a combination of the kinematic information and setup
(Continued)

information associated with a medical procedure to be performed. The control system also generates, by a control system processor, a first registration between a first set of model points of a model of a patient anatomy of interest and a second set of intra-operatively collected captured points of a portion of the patient anatomy of interest, wherein the registration is based on the extracted system information.

18 Claims, 12 Drawing Sheets

(51) Int. Cl.
  *A61B 34/35* (2016.01)
  *A61B 90/00* (2016.01)
  *G06T 3/00* (2006.01)
  *A61B 34/30* (2016.01)
(52) U.S. Cl.
  CPC ...... *G06T 3/0068* (2013.01); *A61B 2034/105* (2016.02); *A61B 2034/2051* (2016.02); *A61B 2034/2059* (2016.02); *A61B 2034/2061* (2016.02); *A61B 2034/301* (2016.02); *A61B 2090/365* (2016.02); *A61B 2090/373* (2016.02)
(58) Field of Classification Search
  CPC ...... A61B 2034/2059; A61B 2090/373; A61B 2034/105; A61B 2034/2051; A61B 2090/3762; A61B 2090/365; A61B 2034/301; A61B 2090/3614; A61B 2034/742; A61B 2034/741; A61B 2090/3735; A61B 2090/374; A61B 2090/368; A61B 2090/371; A61B 2090/376; A61B 2034/2061; G16H 30/40; G16H 20/40; G16H 50/50
  See application file for complete search history.

(56) References Cited

U.S. PATENT DOCUMENTS

| | | | |
|---|---|---|---|
| 6,389,187 | B1 | 5/2002 | Greenaway et al. |
| 6,491,701 | B2 | 12/2002 | Tierney et al. |
| 7,316,681 | B2 | 1/2008 | Madhani et al. |
| 7,772,541 | B2 | 8/2010 | Froggatt et al. |
| 8,010,177 | B2 | 8/2011 | Csavoy et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 10,682,070 | B2 * | 6/2020 | Duindam ............... A61B 5/065 |
| 2006/0013523 | A1 | 1/2006 | Childers et al. |
| 2011/0270084 | A1 | 11/2011 | Choi et al. |
| 2014/0051986 | A1 | 2/2014 | Zhao et al. |
| 2015/0320514 | A1 * | 11/2015 | Ahn ..................... A61B 34/30 |
| | | | 606/130 |
| 2015/0335480 | A1 | 11/2015 | Alvarez et al. |
| 2016/0191887 | A1 | 6/2016 | Casas |
| 2018/0028267 | A1 * | 2/2018 | Onik ...................... A61B 8/12 |
| 2018/0263714 | A1 * | 9/2018 | Kostrzewski .......... A61B 34/76 |

FOREIGN PATENT DOCUMENTS

| | | |
|---|---|---|
| WO | WO-2013038301 A2 | 3/2013 |
| WO | WO-2016025465 A1 | 2/2016 |
| WO | WO-2017030913 A2 | 2/2017 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP18772120.4 dated Sep. 28, 2020, 09 pages.

International Preliminary Report on Patentability for Application No. PCT/US2018/023791, dated Oct. 3, 2019, 13 pages.

* cited by examiner

SYSTEMS AND METHODS FOR INTELLIGENTLY SEEDING REGISTRATION

CROSS-REFERENCE TO RELATED APPLICATIONS

This patent application is the U.S. national phase of International Application No. PCT/US2018/023791, filed Mar. 22, 2018, which designated the U.S. and claims priority to and benefit of the filing date of U.S. Provisional Patent Application 62/474,866, filed Mar. 22, 2017, entitled "SYSTEMS AND METHODS FOR INTELLIGENTLY SEEDING REGISTRATION," which are incorporated by reference herein in their entirety.

FIELD

The present disclosure is directed to systems and methods for conducting an image-guided procedure, and more particularly to systems and methods for displaying pathology data for tissue sampled during an image-guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of patient pads during pre-operative and operative imaging and may disturb the clinical environment or workflow. Systems and methods for performing image-guided surgery with minimal clinical disturbances are needed.

SUMMARY

The embodiments of the invention are best summarized by the claims that follow the description.

However, an exemplary method of registering sets of anatomical data for use in a medical procedure is provided herein. The method may include accessing a first set of model points representing a patient anatomy of interest, intra-operatively acquiring a second set of model points through sensor data representing the anatomy of interest, and extracting system information including kinematic information from a robotic arm of a medical system and/or setup information and generating, by a control system processor, a first registration between the set of model points and the set of surface points based on the extracted system information.

Another exemplary method of registering sets of anatomical data for use in a medical procedure is provided herein and may include accessing a first set of model points representing a patient anatomy of interest and acquiring a second set of model points by visualizing a portion of the patient anatomy of interest with a vision probe. The method may further include extracting system information including kinematic information from a robotic arm of a medical system and/or setup information and generating an initial seed transformation based on the extracted system information prior to generating the first registration. Thereafter, the method may include applying the initial seed transformation to the first set of model points and generating a first registration between the first set of model points and the second set of model points, permitting model and actual information to be viewed and used together.

An exemplary medical system may include a robotic manipulator arm having a plurality of joints to permit movement of the robotic manipulator arm, a vision probe coupled to the robotic manipulator arm such that the vision probe is movable in connection with the robotic manipulator arm, and a control system in communication with the robotic manipulator arm and the vision probe. The control system may be configured to extract system information including kinematic information from a robotic arm of a medical system and/or setup information and generate a first registration between a first set of model points of a patient anatomy of interest and a second set of intra-operatively collected model points of a portion of the patient anatomy of interest based on the extracted system information.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 1A:
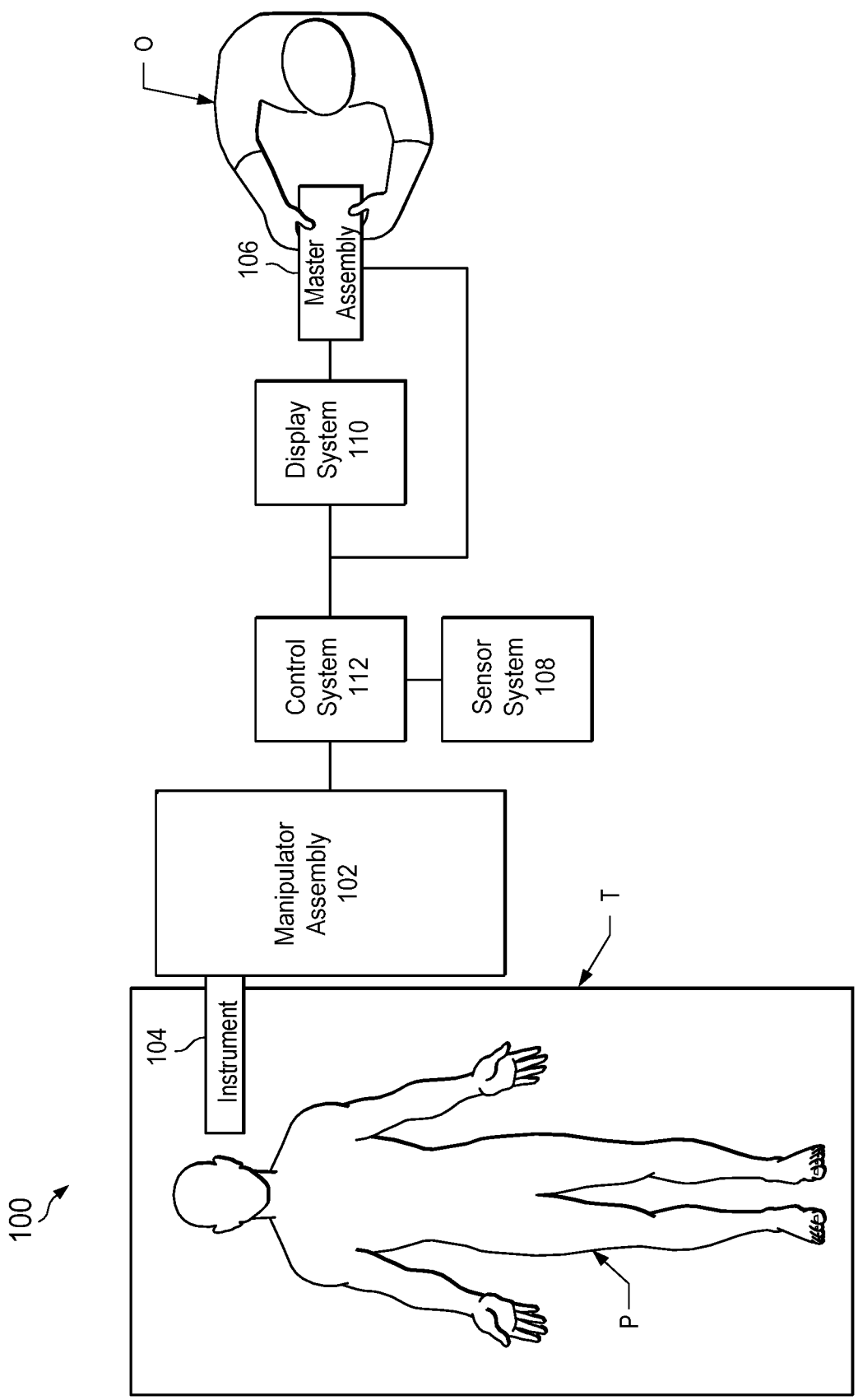
FIG. 1A is a teleoperated medical system, in accordance with embodiments of the present disclosure.

These drawings may be better understood by reference to the following detailed description.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a operator O as illustrated in FIG. 1) to view the interventional site and to control teleoperational manipulator assembly 102.

Master assembly 106 may be located at a operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the anatomical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of an anatomical site and provides the image to the operator or operator O through one or more displays of medical system 100, such as one or more displays of display system 110. The concurrent image may be, for example, a two or three dimensional image captured by an endoscope positioned within the anatomical site. In some embodiments, the visualization system includes endoscopic components that may be integrally or removably coupled to medical instrument 104. However in some embodiments, a separate endoscope, attached to a separate manipulator assembly may be used with medical instrument 104 to image the anatomical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Display system 110 may also display an image of the anatomical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a operator that is physically manipulating medical instrument 104.

In some examples, display system 110 may present images of a anatomical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided medical procedures, display system 110 may display a virtual navigational image in which the actual location of medical instrument 104 is registered (i.e., dynamically referenced) with the preoperative or concurrent images/model. This may be done to present the operator O with a virtual image of the internal anatomical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the anatomical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal anatomical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided medical procedure. Virtual navigation using the virtual visualization system may be based upon reference to an acquired preoperative or intraoperative dataset of anatomic passageways. The virtual visualization system processes images of the anatomical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded anatomical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the medical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 1B:
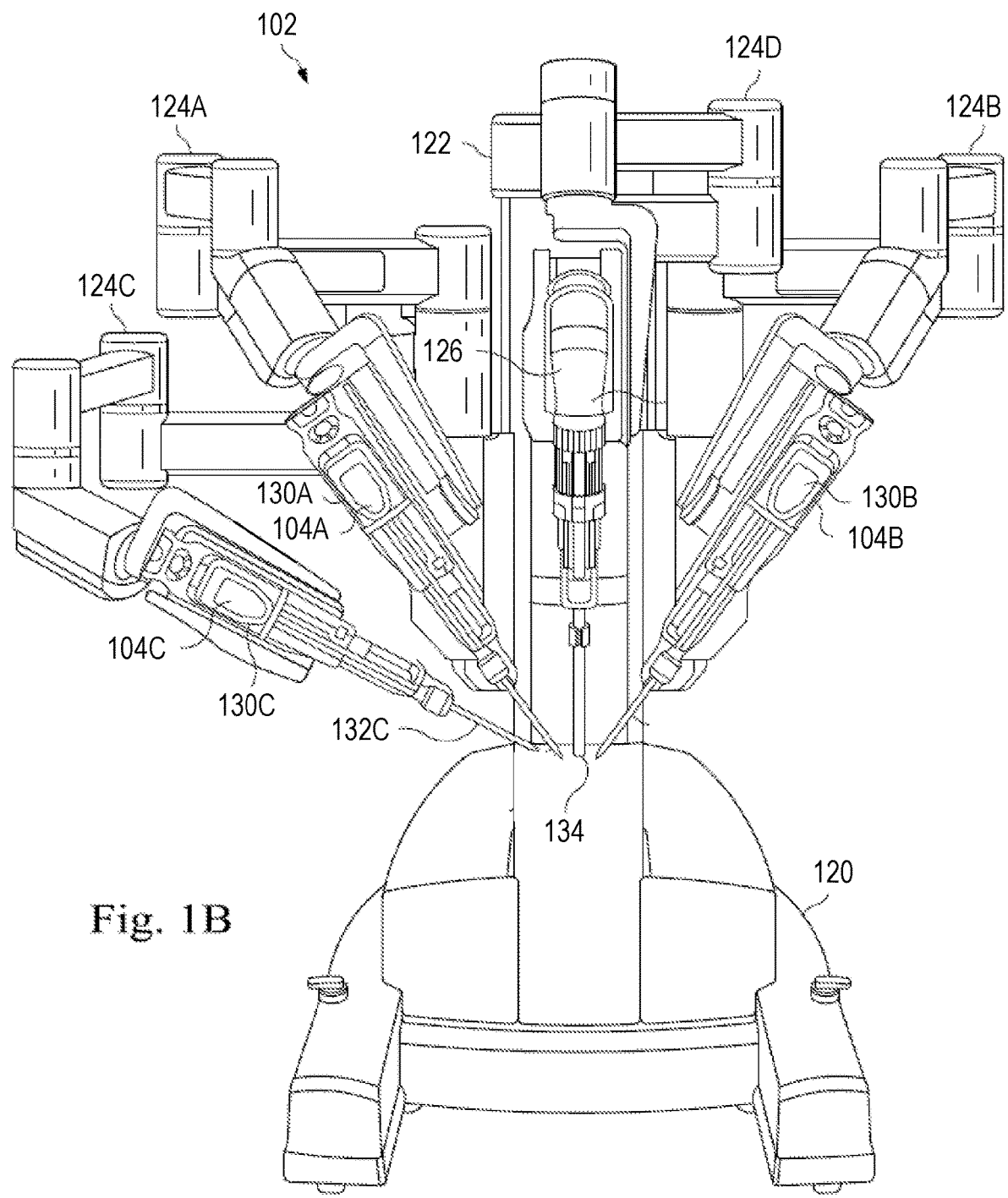
FIG. 1B illustrates a front elevation view of aspects of an exemplary teleoperational assembly according to embodiments of the present disclosure.

FIG. 1B is a front elevation view of some embodiments of the teleoperational assembly 102 shown in FIG. 1A. The assembly 102 includes a base 120 that rests on the floor, a support tower 122 that is mounted on the base 120, and several arms that support medical tools. As shown in FIG. 1B, arms 124A, 124B, 124C are instrument arms that support and move the medical instruments used to manipulate tissue, and arm 124D is a camera arm that supports and moves the endoscope. FIG. 1B further shows interchangeable medical instruments 104A, 104B, 104C mounted on the instrument arms 124A, 124B, 124C, respectively, and it shows an imaging system 126 mounted on the camera arm 124D. The imaging system 126 may be a stereo endoscope for capturing stereo images of the anatomical site and providing the separate stereo images to the display system 110 of FIG. 1A. Other implementations of the imaging system 126 are discussed herein. Knowledgeable persons will appreciate that the arms that support the instruments and the camera may also be supported by the base 120 or another base platform (fixed or moveable) mounted to a ceiling or wall, or in some instances to another piece of equipment in the operating room (e.g., the operating table T). Likewise, they will appreciate that two or more separate bases may be used (e.g., one base supporting each arm).

As is further illustrated in FIG. 1B, the instruments 104A, 104B, 104C, and the imaging system 126 include instrument interfaces 130A, 130B, 130C, and 130D, respectively, and instrument shafts 132A, 132B, 132C, and 132D, respectively. In some embodiments, the teleoperational assembly 102 may include supports for cannulas that fix the instruments 104A, 104B, 104C, and the imaging system 126 with respect to the cannulas. In some embodiments, portions of each of the instrument arms 124A-D may be adjustable by personnel in the operating room in order to position the instruments 104A-C and the imaging system 126 with respect to a patient. Other portions of the arms 124A, 124B, 124C, and 124D may be actuated and controlled by the operator at an operator input system. The medical instruments 104A, 104B, 104C, and imaging system 126, may also be controlled by the operator O at the operator input system, such as the master assembly 106.

Figure 2A:
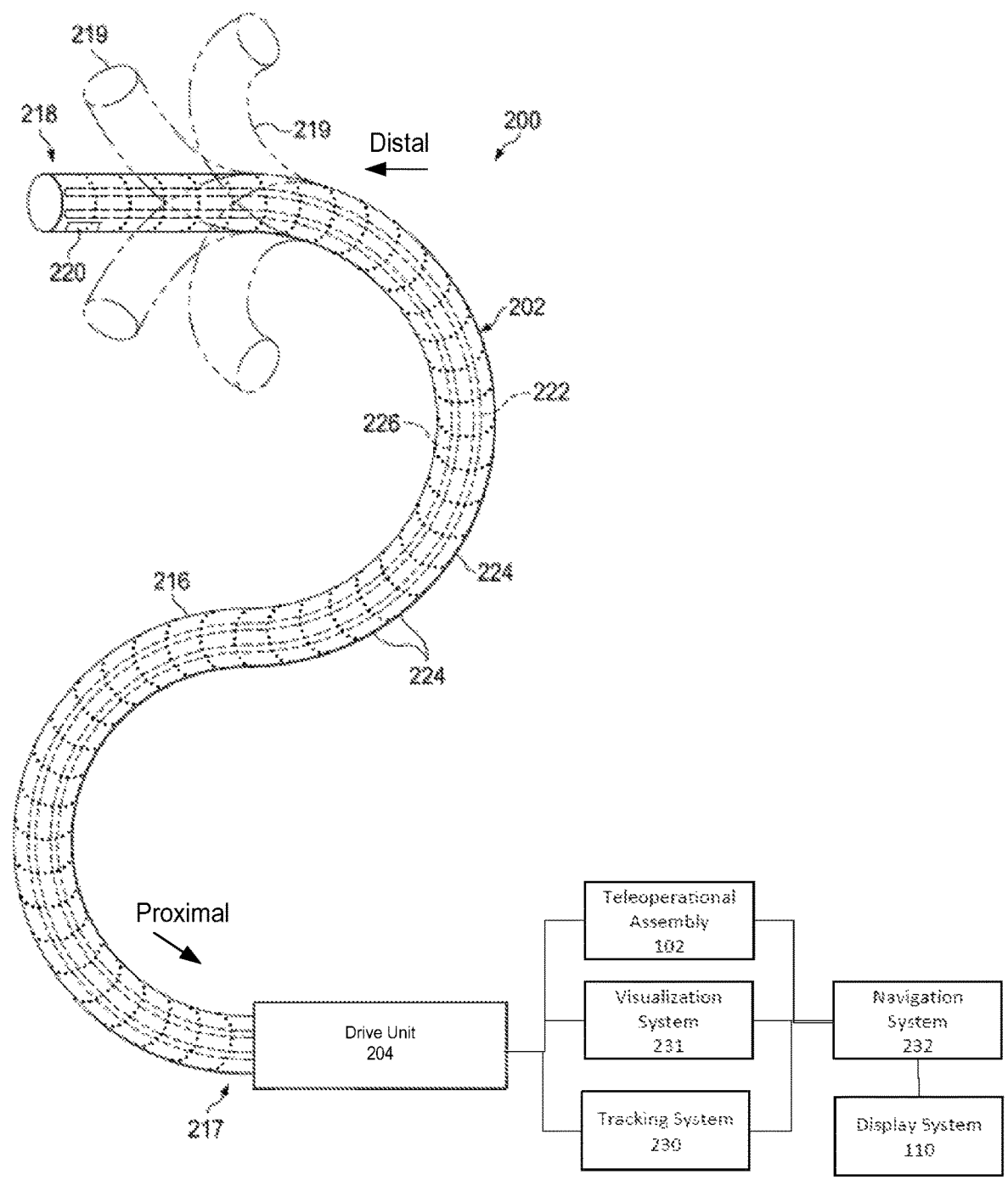
FIG. 2A illustrates a medical instrument system utilizing aspects of the present disclosure.

FIG. 2A illustrates a medical instrument system 200, which may be an embodiment of the medical instrument system 104 and or the manipulator assembly 102 in an image-guided medical procedure performed with some embodiments of the teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument body or housing 204. The catheter system 202 includes an elongated flexible catheter body 216 having a proximal end 217 and a distal end 218 or tip portion. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive a medical instrument 226. Medical instruments may include, for example, image capture probes, biopsy instruments, laser ablation fibers, or other surgical, diagnostic, surgically diagnostic, and/or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target anatomical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a medical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In the embodiment of FIG. 2A, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 2B:
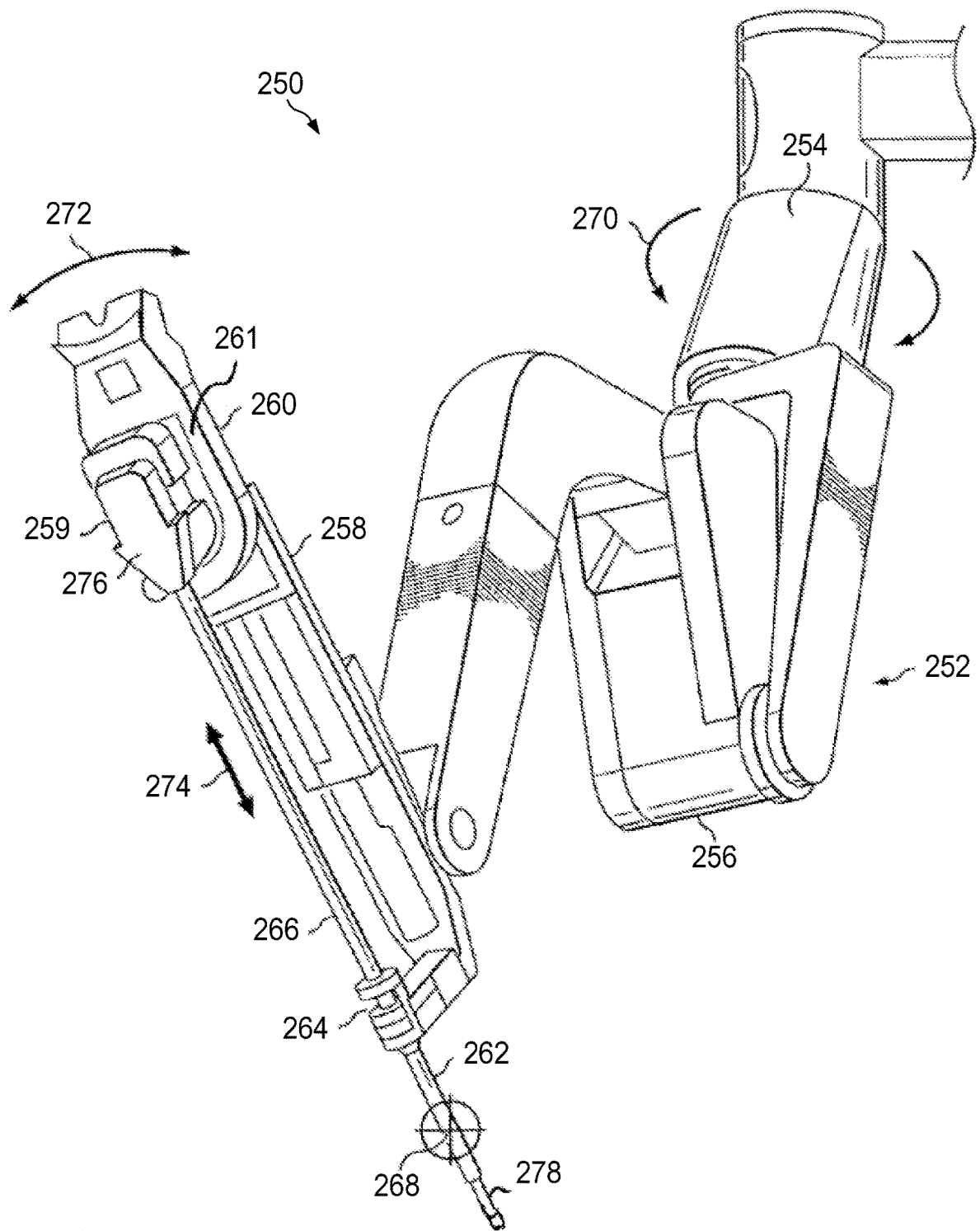
FIG. 2B illustrates another medical instrument system utilizing aspects of the present disclosure.

FIG. 2B illustrates a medical instrument system 250, which may be used as the medical instrument system 104 in a medical procedure performed an embodiment teleoperational medical system 100 as shown in FIG. 1B. Additionally or alternatively the medical instrument system 250 may be used to gather (i.e., measure) a set of data points corresponding to locations with patient anatomic passageways and surfaces of patient anatomical features, such as an organ or a body cavity. FIG. 2B is a perspective view of a manipulator 252 of a control arm that may be mounted to the assembly 102. Sterile drapes and associated mechanisms that are normally used during surgery are omitted for clarity. The manipulator 252 includes a yaw servo actuator 254, a pitch servo actuator 256, and an insertion and withdrawal ("I/O") actuator 258. A medical instrument 259 is shown mounted at an instrument spar 260 including a mounting carriage 261. An illustrative straight cannula 262 is shown mounted to cannula mount 264. Other types of cannulas may be used, as is discussed in more detail below. Shaft 266 of instrument 259 extends through cannula 262. Manipulator 252 is mechanically constrained so that it moves instrument 259 around a stationary remote center of motion 268 located along the instrument shaft. Yaw actuator 254 provides yaw motion 270 around remote center 268, pitch actuator 256 provides pitch motion 272 around remote center 268, and I/O actuator 258 provides insertion and withdrawal motion 274 through remote center 268. The manipulator 252 may include an encoder to track position and velocity associated with servo positions along the insertion axis of the I/O actuator 258 and other encoders to track position and velocity of yaw servo actuator 254 and pitch servo actuator 256 The remote center 268 may be locked at the incision in the patient's body wall during surgery and to allow for sufficient yaw and pitch motion to be available to carry out the intended medical task. Alternatively, the remote center of motion may be located outside of the body to allow a greater range of motion without contacting the patient. Knowledgeable persons will understand that motion around a remote center of motion may be constrained by the use of software or by a physical constraint defined by a mechanical assembly.

Matching force transmission disks in mounting carriage 261 and instrument force transmission assembly 276 couple actuation forces from actuators in manipulator 252 to move various parts of instrument 259 in order to position and orient a probe 278 mounted at the distal end of the curved shaft 266. Such actuation forces may typically roll instrument shaft 266 (thus providing another degree of freedom (DOF) through the remote center 268). The amount of roll may be tracked via an encoder. Embodiments of force transmission assemblies are provided in U.S. Pat. No. 6,331,191 (filed Oct. 15, 1999; disclosing "Surgical Robotic Tools, Data Architecture, and Use") and U.S. Pat. No. 6,491,701 (filed Jan. 12, 2001; disclosing "Mechanical Actuator Interface System for Robotic Surgical Tools") which are incorporated herein by reference in its entirety. In alternative embodiments, the instrument 259 may include a wrist at the distal end of the shaft that provides additional yaw and pitch DOF's. The probe 278 may be, for example, a vision probe, such as a stereoscopic imaging catheter having a stereoscopic camera or a three-dimensional, structured light scanner that can be introduced and positioned via the manipulator 252.

Some embodiments of instrument systems that are within the scope of the present disclosure include instruments that combine aspects of the instrument system 200 of FIG. 2A and aspects of the instrument system 250 of FIG. 2B. For example, some instrument systems that may be used in the medical system 100 may include a flexible catheter, like the flexible catheter body 216 of FIG. 2A, supported by one or more of the arms 124A-D of FIGS. 1A and 2B. As a more specific example, an arm like the arm 124A may provide the insertion and withdrawal motion 274 for a flexible device like the flexible catheter body 216. In such embodiments, the control system 112 may use sensor information from sensors disposed on, in, or along the arm or arms and from sensors disposed on, in, or along the catheter to determine a position and orientation of any portion of the catheter body 216, such as a distal end thereof, which may include an imaging component or another end effector.

Figure 3A:
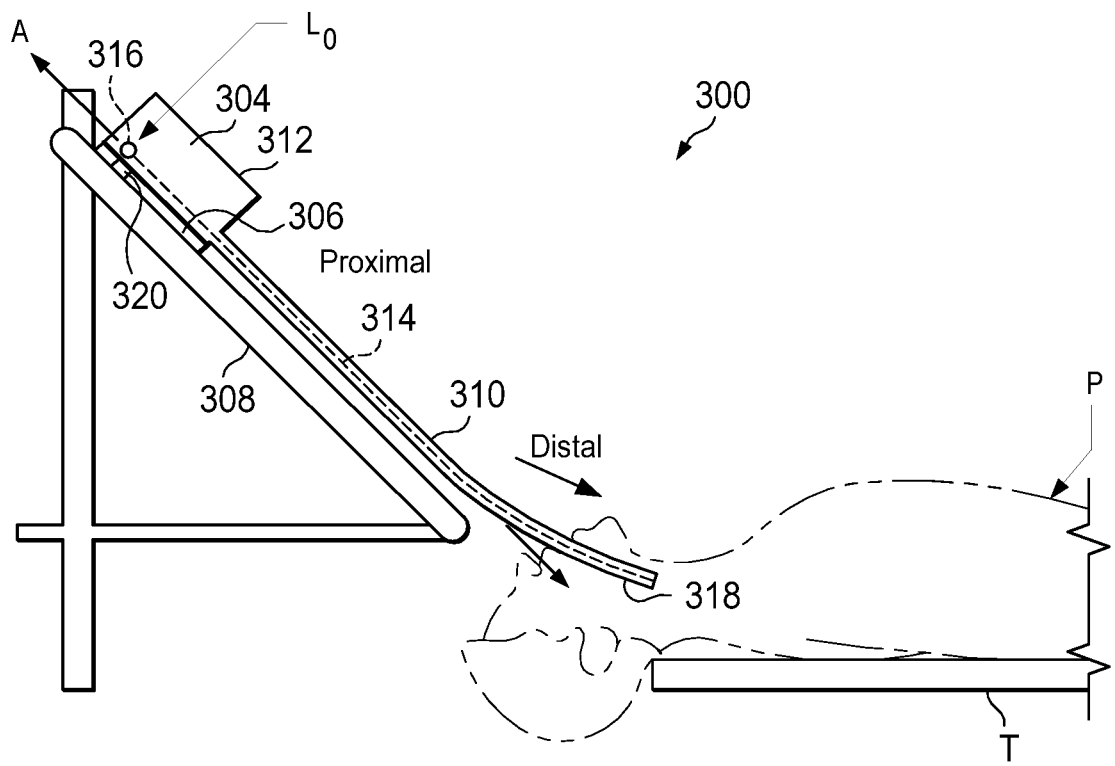
FIGS. 3A and 3B are side views of a patient coordinate space including a medical instrument mounted on an insertion assembly according to an embodiment of the present disclosure.
Figure 3B:
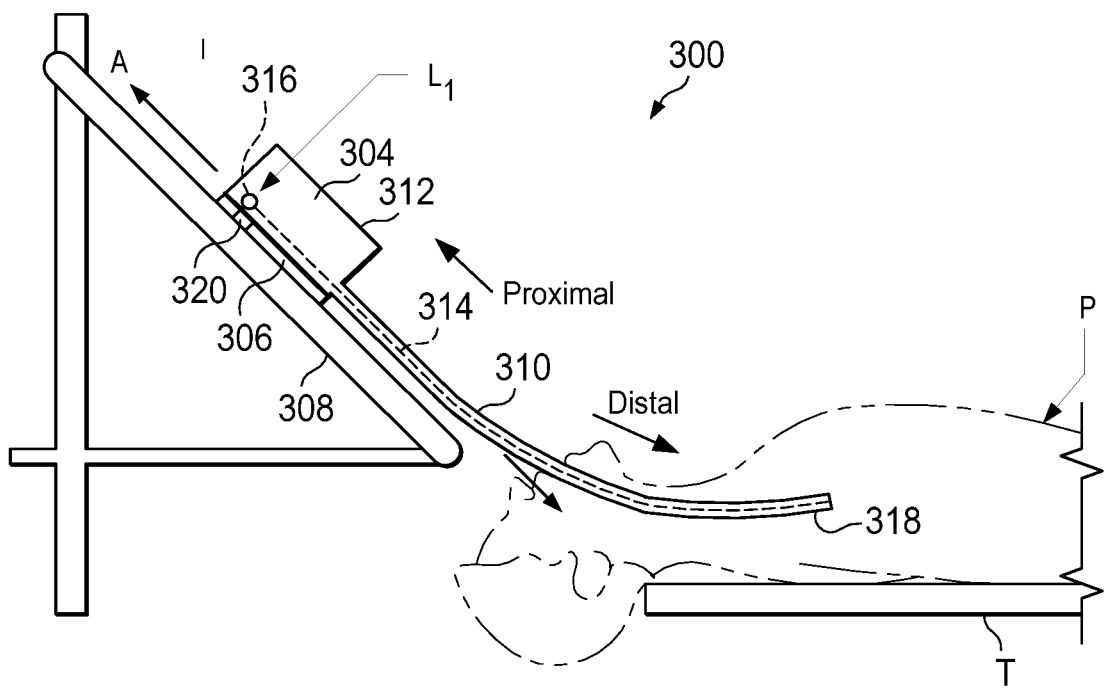

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200 of FIG. 2A. Alternatively, the point gathering instrument could itself be a rigid instrument coupled to the proximal rigid instrument body or a flexible catheter which could be actuated into a rigid state.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

Figure 3C:
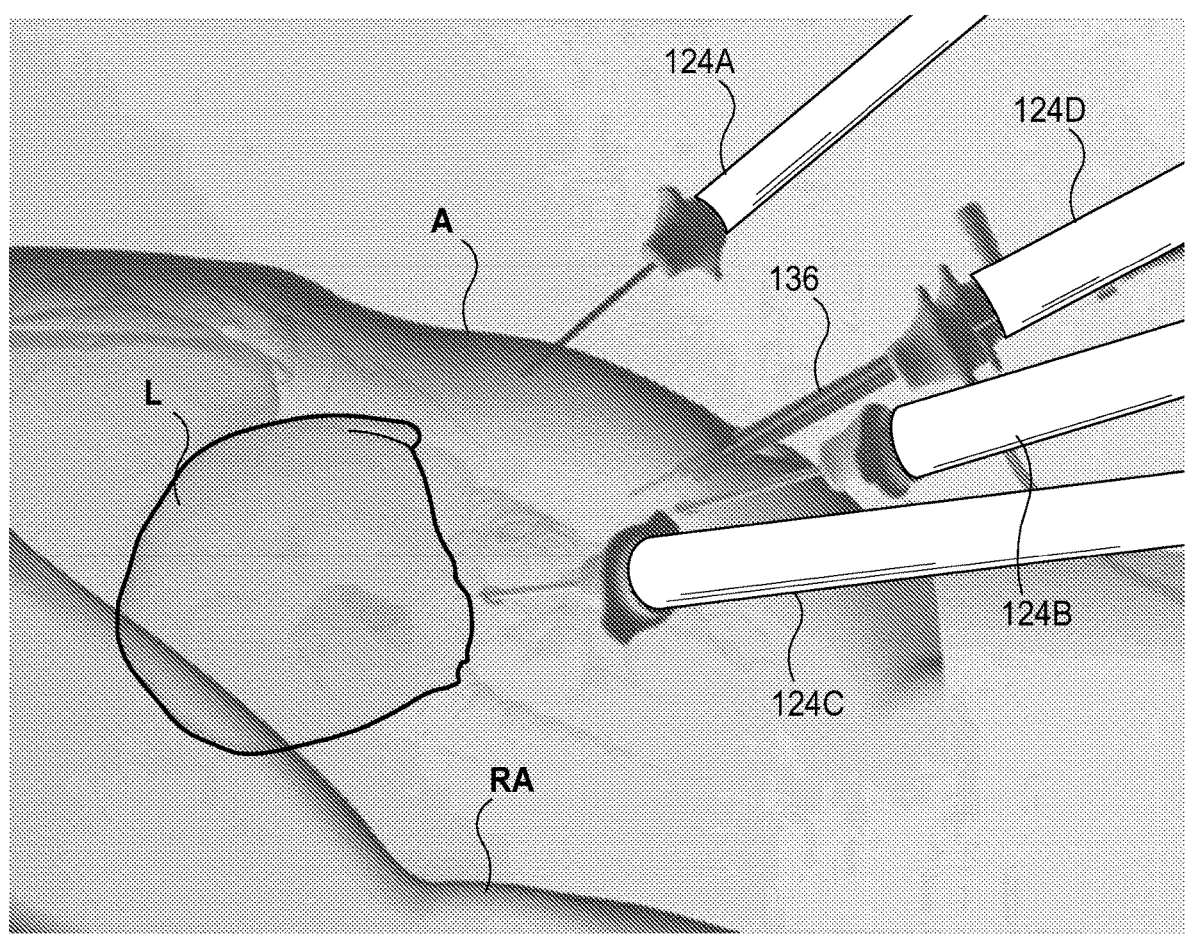
FIG. 3C is a side view of a patient coordinate space including a plurality of instruments positioned for an exemplary procedure according to an embodiment of the present disclosure.

FIG. 3C is a perspective view of a patient P undergoing a medical procedure according to some aspects of the present disclosure. As illustrated, the medical procedure is a liver surgery. The right arm RA and abdomen A of the patient P are shown transparently so that the liver L can be observed more clearly. FIG. 3C further illustrates the arms 124A-D of FIG. 1B, with the instrument shafts 132A-C of medical instruments 130A-C protruding into the abdomen A. To provide better access to the medical instruments 130 A-C within the abdomen A, one of the instruments 130A-C may provide for insufflation of the abdomen A. FIG. 3C depicts the imaging probe 136 of the imaging system 126 as inserted within the abdomen A to provide for visualization and/or registration of organs and tissues within the abdomen A. In particular, the imaging probe 136 has been positioned and oriented by the arm 124D to image at least a portion of the liver L. The imaging probe 136 may include sensors to provide one or more imaging modalities. For example, the imaging probe 136 may include a stereoscopic imaging camera, a structured light emitter, a LIDAR emitter/detector system, or combinations thereof.

Figure 4:
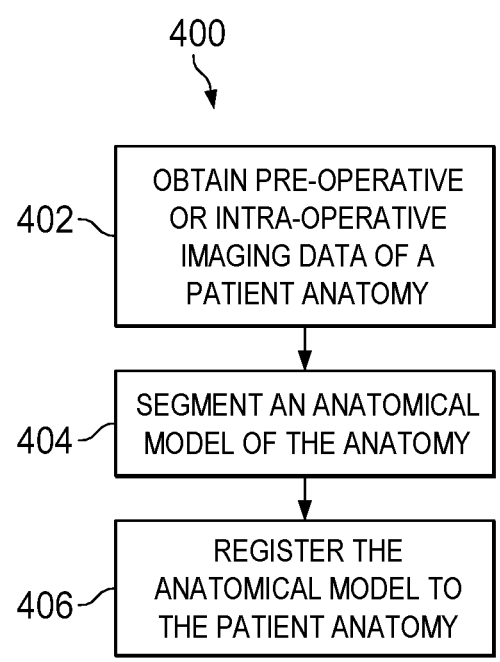
FIG. 4 is a flowchart illustrating a method general of registering a model to a corresponding anatomical structure to provide guidance in an image-guided medical procedure according to an embodiment of the present disclosure.

FIG. 4 is a flowchart illustrating a general method 400 for use in an image-guided medical procedure. At a process 402, pre-operative or intra-operative image data is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent any anatomical structure of patient P. For example the image data may represent the interior passageways of the lungs or the exterior surface of the liver.

At a process 404, computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 406, the anatomic model data is registered to the patient anatomy prior to and/or during the course of an image-guided medical procedure on the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique described in detail at FIG. 5 and elsewhere in this disclosure. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below perform registration based upon ICP, or another point set registration algorithm, and the calibrated movement of a point gathering instrument with a fiber optic shape sensor, thus eliminating or minimizing disruptions in the surgical environment. Other registration techniques may be used to register a set of measured points to a pre-operative model or a model obtained using another modality. In the embodiments described below, EM sensors on the patient and the instrument and optical tracking systems for the instrument may be eliminated.

Figure 5:
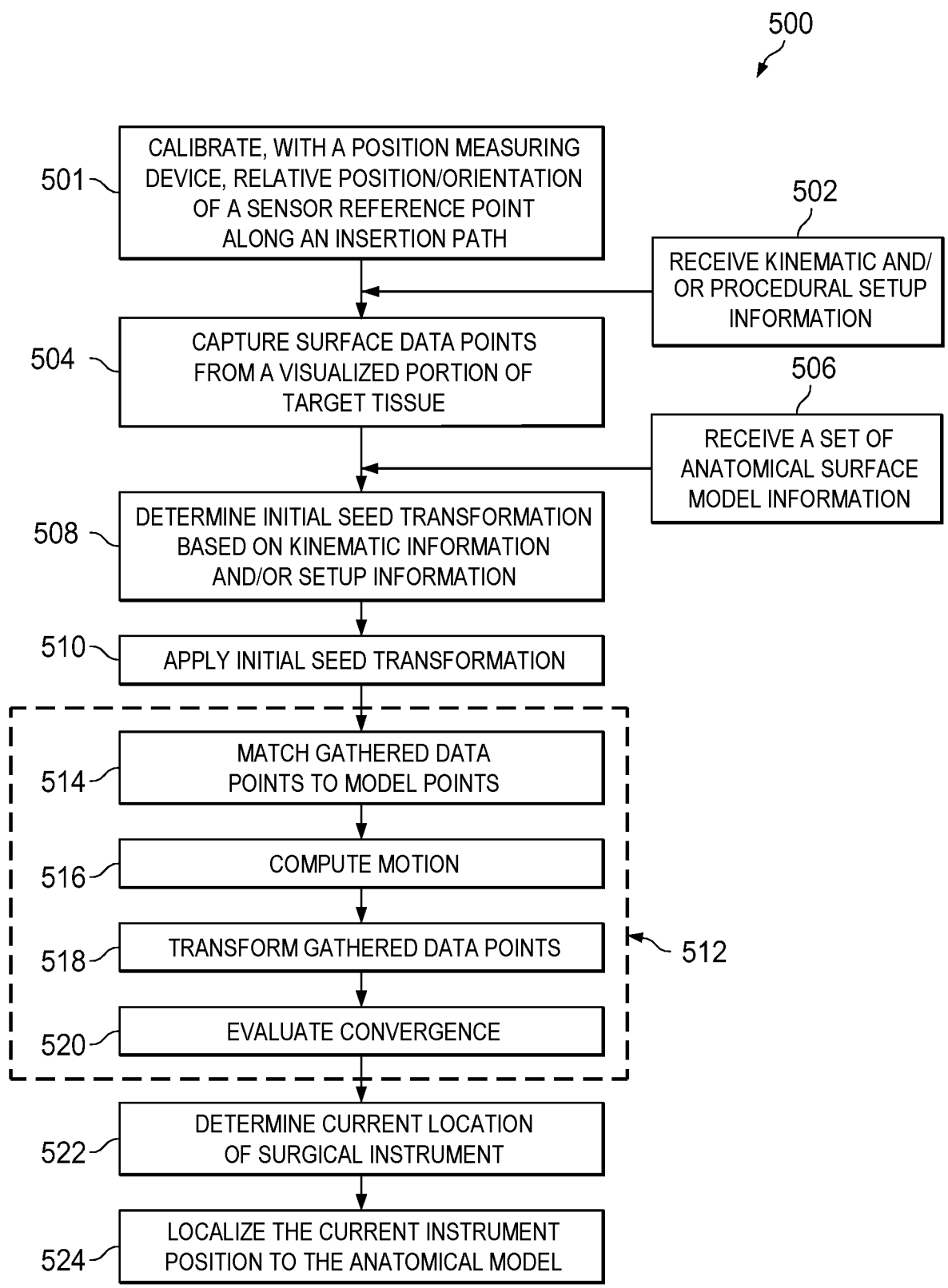
FIG. 5 is another flowchart illustrating a method of registering a model to a corresponding anatomical structure to provide guidance in an image-guided medical procedure according to an embodiment of the present disclosure.

FIG. 5 is a flowchart illustrating a method 500 used to provide guidance to a clinician in an image-guided medical procedure on the patient P in the surgical environment shown in FIG. 1, according to some embodiments of the present disclosure. The method 500 is illustrated in FIG. 5 as a set of blocks, steps, operations, or processes. Not all of the illustrated, enumerated operations may be performed in all embodiments of the method 500. Additionally, some additional operations that are not expressly illustrated in FIG. 5 may be included before, after, in between, or as part of the enumerated processes. Some embodiments of the method 500 include instructions corresponded to the processes of the method 500 as stored in a memory. These instructions may be executed by a processor like a processor of the control system 112.

The method 500 further includes operations that provide a method for generating and applying an initial seed transformation based on extracted kinetic information from the manipulator 252 or other arm having a kinematic chain and/or based on workflow information associated with the procedure to be performed. The method 500 may be implemented as part of a workflow managed by the control system 112 to enable the operator O to more effectively and efficiently treat patients like the patient P.

Some embodiments of the method 500 may begin at a process 501, in which a calibration procedure is performed to calibrate, with a position measuring system such as the system of encoders or shape sensors in the arms 124A-D of FIG. 1B, a relative position and/or orientation of an imaging system, like the imaging system 126. For example, the tip of the imaging system 126 and be placed at one or more known locations in the surgical environment and the measurements from the encoders or another position measurement system of the arm 124D may be observed to ensure correspondence between the measured position or kinematic information and the actual position and pose of the arm 124D.

At operation 502, position and pose information associated with the system 100 may be extracted and received by the control system 112. For example, the control system 112 may interrogate encoders, potentiometers, shape sensors disposed within one or more of the arms 124A-D. For example, the control system 112 may receive kinematic information from the arm 124D which supports the imaging system 126. This information may be received while the arm 124D is being controlled by the operator O to provide visualization of the patient P, specifically of an interventional site within the patient P. Additionally, the control system 112 may receive procedural setup and/or workflow information associated with the procedure to be performed. For example, the operator O may interact with a user interface to select a particular procedure such as a lung biopsy, prostatectomy, or liver surgery. These and many other procedures may have corresponding workflows stored in the control system 112. Each workflow may contain information including an indication of the procedure to be performed, an ideal approach to a target anatomy, and a listing of steps to be undertaken during normal performance of such procedures. The control system 112 may communicate a step in the workflow to the operator O to help ensure proper performance of the procedure and to provide appropriate information and appropriate options to the physician O at appropriate times. Accordingly, the control system 112 may receive information describing a pose of the arm 124D relative to the patient P and receive information scribing the type of procedure being performed and the step in that procedure being undertaken at any given time.

In some embodiments, the kinematic information received at operation 502 may be received from a fiber optic shape sensor extending through the arm 124D and into or through the imaging probe 136. Accordingly, the kinematic information may include a series of three-dimensional positions of the arm 124D or a model generated from measured angles and known or measured lengths of the arm 124D. Further, some embodiments of the operation 502 may receive information from a flexible catheter inserted into the anatomical passageways of the patient to deliver medical instruments to a distal tip thereof.

Figure 6A:
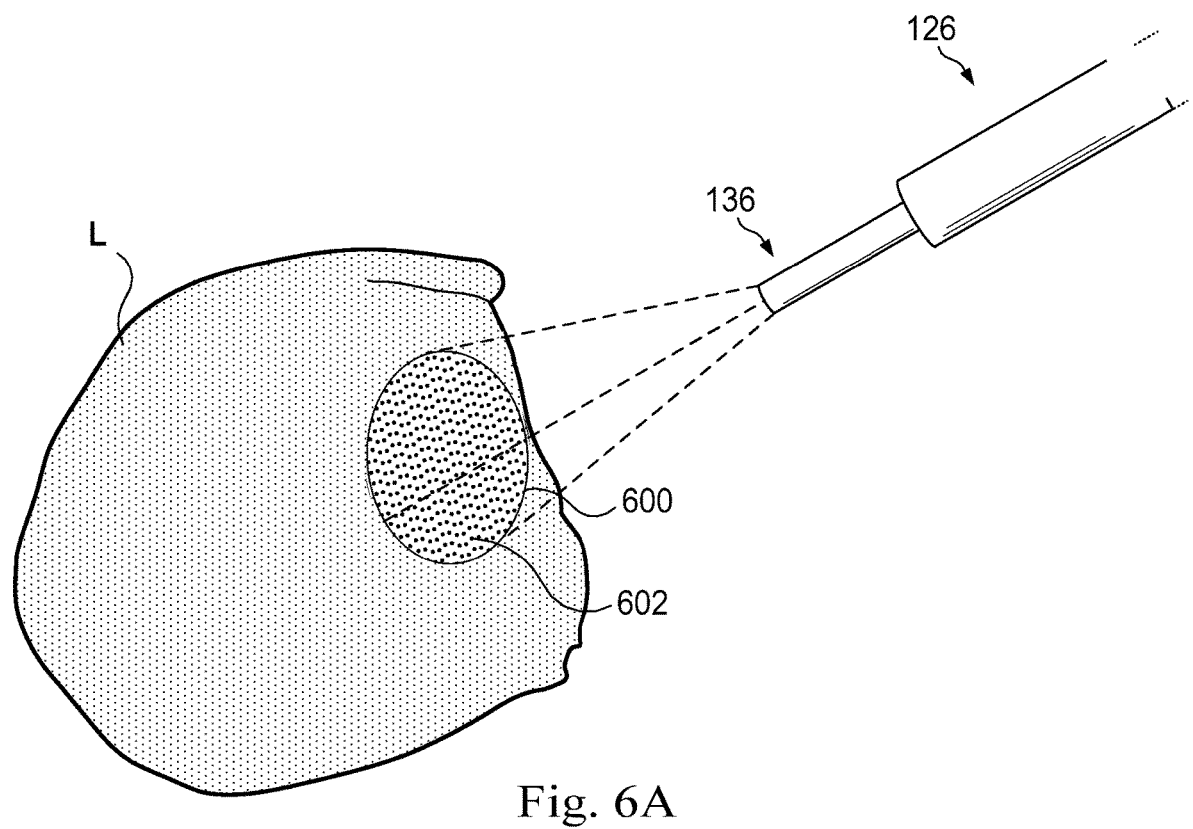
FIG. 6A illustrates an organ of FIG. 3C being imaged by a vision probe according to aspects of the present disclosure.

As described above, FIG. 3C shows a patient P undergoing liver surgery. FIG. 3C illustrates the arms 124A-D, with the instrument shafts 132A-C of medical instruments 130A-C protruding into the abdomen A. FIGS. 3C and 6A depicts the imaging probe 136 of the imaging system 126 as inserted within the abdomen A to provide for visualization of organs and tissues within the abdomen a. In particular, the imaging probe 136 is aligned by the arm 124D to image a portion of the liver L.

Figure 6B:
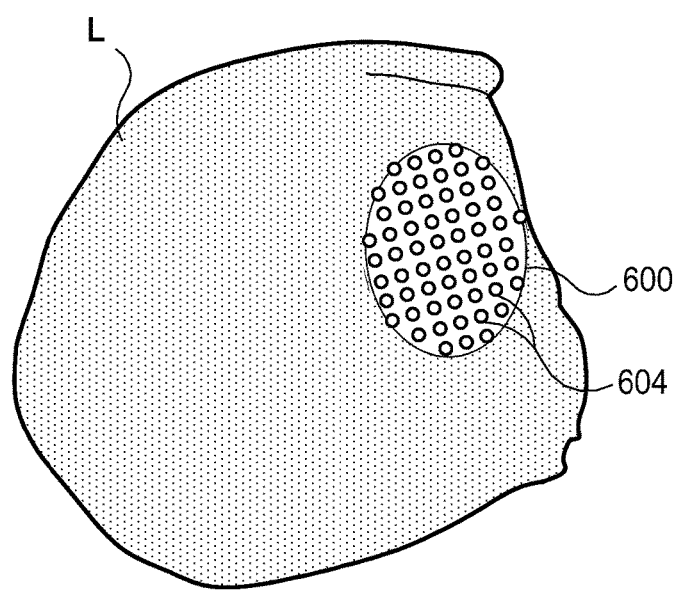
FIG. 6B depicts a set of three-dimensional points that represent the organ of FIG. 6A according to aspects of the present disclosure.

Returning to the method 500, at operation 504, the imaging probe 136 may be activated by the control system 112 to capture surface data points from a visualized portion of target tissue. As shown in FIG. 6A, the imaging probe 136 may be a structured light probe that emits light in a way that can be interpreted to determine depth information of the illuminated portion 600. In some embodiments, the illuminated portion 600 may be only a limited portion of a field of view visualized by the imaging probe 136 or another component of the image system 126. For example, and emitter of the imaging probe 136 may project an array or grid of dots 602. These dots may be read by a detector of the imaging probe 136 and interpreted to provide three-dimensional information describing the portion of the surface of the liver L included in the illuminated portion 600. For example, FIG. 6B depicts a plurality of three-dimensional points 604 that characterize a surface or volume of the illuminated portion 600. The control system 112 may process the three-dimensional information to generate the plurality of data points 604 to facilitate registration of the model to the liver L. In other embodiments, other systems, such as a LIDAR system may be used to generate a set of data points that describe the surface of the liver L.

Figure 7:
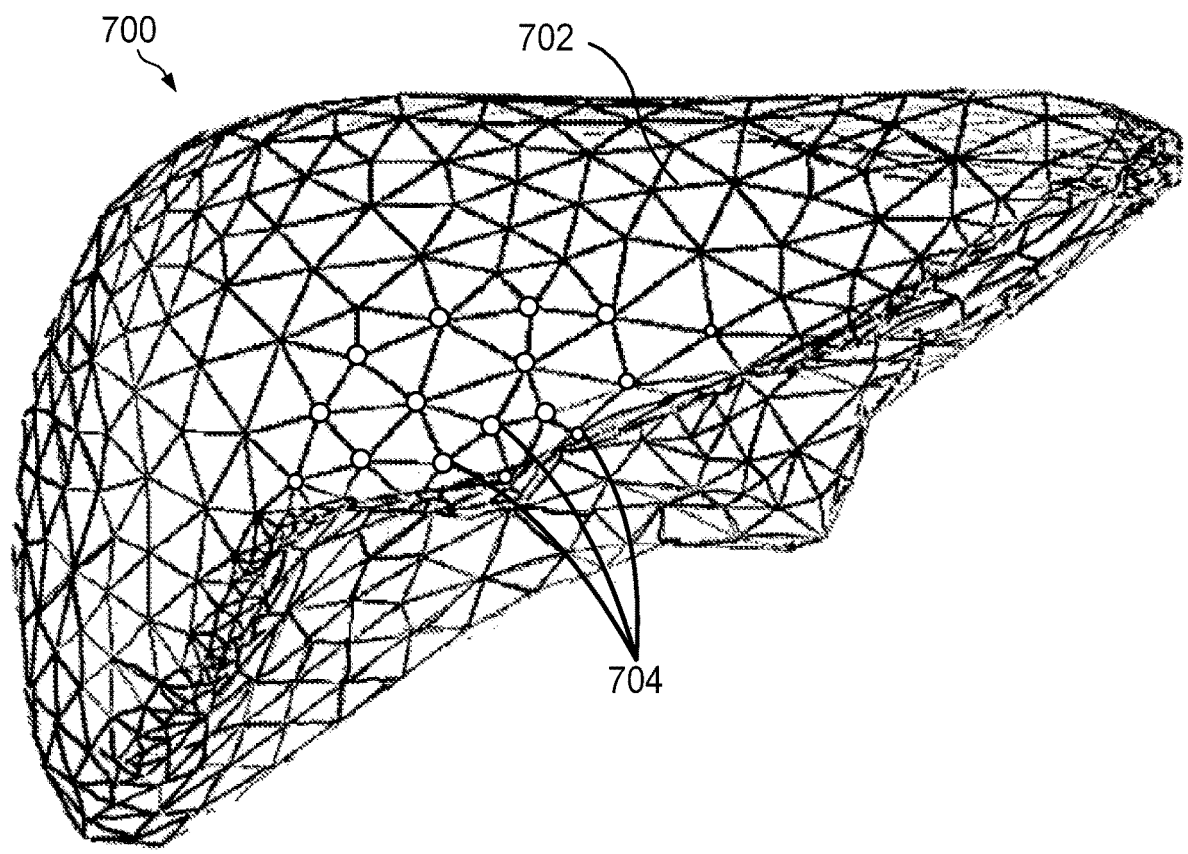
FIG. 7 illustrates an anatomic model representing the organ of FIGS. 6A and 6B.

At operation 506, a three-dimensional topology of the liver L may be received by the control system 112. The model may be a surface model, such as the mesh surface model shown in FIG. 7. FIG. 7 depicts a model 700 of the liver L of the patient P. While illustrated in this example as a surface model, it should be understood that a set of modal points can be represented as any number of two-dimensional or three-dimensional anatomical topology including wireframe models, volumetric models, etc. As illustrated, the exemplary model 700 is a mesh model, but other embodiments of the operation 508 may include the receipt of a volumetric model that represents the liver L as a set of voxels. The set of voxels may be processed to produce a surface or a set of points characterizing a surface or topology of an anatomical structure, like the liver or the interior passageways of the lungs. In some embodiments, the model 700 may be received as a set of model points in three dimensions that describe the surface of the liver L. In other embodiments, the control system 112 receives the volumetric model or the surface model, or another model of the liver L and process the model to obtained a set of model points. The points may be obtained by collection and processing of pre-operative or intra-operative image data from imaging technologies such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. For example, the control system 112 may receive the model 700 and find intersection points in the surface mesh 702. The control system 112 may extract three-dimensional points 704 from the intersection points and/or from a center of each triangle or unit-shape of the mesh 702.

These extracted model points may be generated as part of operation 506. Other three-dimensional models may be used in other embodiments.

At operation 508, an initial seed transformation is determined based on the information from the manipulator assembly 102 and from procedural setup information associated with the particular procedure to be performed. Accordingly, the initial seed transformation may be on extracted system information including extracted kinetic information from the manipulator 252 or another arm having a kinematic chain and/or based on setup information associated with the procedure to be performed, such as what type of procedure is to be performed, whether the procedure is to be performed on a left or right side of the patient, how the patient is oriented relative to the manipulator assembly 102 (e.g. which direction a patient head and feet are positioned relative to the manipulator assembly 102), the point of entry (e.g. is access to target anatomy through the stomach, back, mouth, leg such as through the femoral artery), the angle of entry, the position of the vision probe 278 relative to other medical instruments, etc. Some of this system information may be determined from the instrument being used; however, other information such as the point of entry of side of the patient is provided to the control system 112 by the operator O during the procedure setup. In order to register the captured surface points 604 or other modal points with model information, such as the model points 704, an initial seed transformation is applied to one or both sets of points to bring the model into the same reference frame as the liver L.

In order to register surface points collected using the probe 278 of the manipulator 252 of FIG. 2B, kinematic information may be used. For example, the encoders may indicate a particular position associated with the yaw servo actuator 254, the pitch servo actuator 256, and the I/O actuator 258. This information may be used to identify the angle at which the visualized portion or illuminated portion 600 of the liver L (as seen in FIG. 6A) is being observed by the probe 278. The orientation or roll of the distal end of the probe 278 may be obtained from an encoder, whereby the orientation of the probe 278 relative to the operating environment, including the table may be used in the registration of points. For example, if a vision sensor disposed at the end of the probe 278 is oriented at 35° with respect to the horizon defined by the table, an initial seed transformation may orient the set of points 704 (of FIG. 7) more closely to the orientation defined by the table or any other defined orientation within the surgical environment. Additionally, a distance between the tip of the probe 278 and the surface of the liver L may be detected using the stereoscopic properties of the probe 278. The angle of observation and the distance between the probe 278 and the illuminated portion 600 may be used to generate the initial seed transformation to commence registration of the surface model 700 with the captured data points 604 of the liver L. For example, a transformation matrix may be generated and applied to the points 704 to register them to the three-dimensional points 604 obtained by visualizing the liver L, as shown in FIGS. 6A and 6B. The transformation matrix may include factors that provide for the rotation of the points 704 and the translation of those points 704 in three dimensions toward the points corresponding to the surface in the illuminated portion 600 of the liver L. In some implementations, the translation provided by the transformation matrix may be based on a user input.

Additionally, the system 100 may be configured to guide an operator, such as the operator O via a setup, including procedure setup steps, associated with a particular procedure. The surgeon may interact with the system 100 to select a particular procedure from among a plurality of options. The specific procedure that is selected, the anatomy to be targeted, the anatomical approach to the patient's body (e.g. a left or right approach to anatomy, angle of incision based on target anatomy, etc.), and the step in an associated workflow may also be used in determining the initial seed transformation to be applied to the two sets of points, like points 1502 and points 1516, that are to be registered. The operator O may interact with the system 100 to select a particular procedure from among a plurality of options. For example, the operator O may select a liver surgery from a plurality of medical procedure options.

The procedure that is selected and the step in the associated setup may also be used in determining the initial seed transformation to be applied to one of the two sets of points, like points 604 and 704, that are to be registered together. For example, if procedural step in a workflow is an incision step in which an incision is to be made in tissue, the system 100 may indicate that subsequently collected three-dimensional surface information (new points 704) is not to be used for registration because the incision may alter the surface of the organ or tissue in a way that does not correspond to the pre-operative image data and so would result in a poor quality registration or the degradation of an previously-performed registration. Alternatively, the control system 112 may require that a different portion of the organ or tissue be used for registration. This may require the arm 124D to be moved so that the probe tip 278 is oriented to collect surface data in an unaltered region of the organ or tissue. This may result in overriding a default setting that periodically or on an event-driven basis updates the registration. The setup may indicate that the organ or tissue is visualized from a specific angle at a particular step in the workflow and may specify a general angle, orientation, and point of entry. For example, the workflow may indicate that a port is to be used proximate the naval of the patient or that one or more instruments are to be inserted through a natural orifice of the body, such that an estimate of the angle of the instrument relative to the target organ or tissue can be obtained. During that step, the angle may be used in performing in the initial seed transformation, which may be applied to the model points 704 to bring them into a patient coordinate space defined by the surgical environment. Alternatively, the initial seed transfer may be applied to the collected surface points 604 to bring the points 604 into a model space. Regardless of which points the transform is applied to, the initial transform provides the first step to bring the two sets of points into a common space, so that actual and modeled information can be used jointly by the operator O.

Additionally, relative positions between multiple instruments may also be included in the setup information. Such information may be obtained from the current procedural step in a workflow, as well as immediately upon selection of the setup from a menu of potential procedural setup information.

In some embodiments, a force sensor may be used to physically contact and organ or tissue. The kinematic information from the encoders of the manipulator 252 may be used along with the information from the force sensor to indicate a position of the target surface that is to be registered with the model 700. The force sensor data may provide surface points, like the surface points 604 of FIG. 6B. In some embodiments, a vision sensor may be used to determine whether contact has been made. For example, when the vision sensor approaches the target tissue and overall light signal obtained from the vision sensor may decrease towards zero, indicating contact between the vision sensor and the target tissue. Knowledge of the kinematic information may be used to determine a pose of a force sensor or a vision sensor at the time of contact. In some embodiments, a point may be collected based on the detection of contact. For example the distal end 218 of the flexible catheter body 216 may include contact sensor. The position of the distal end 218 when contact is made between the distal end 218 and an anatomical surface may be extracted from shape or position sensors included on the catheter body 216. The anatomical surface may be contacted repeatedly to obtain a set of points for use in registration.

Figure 8A:
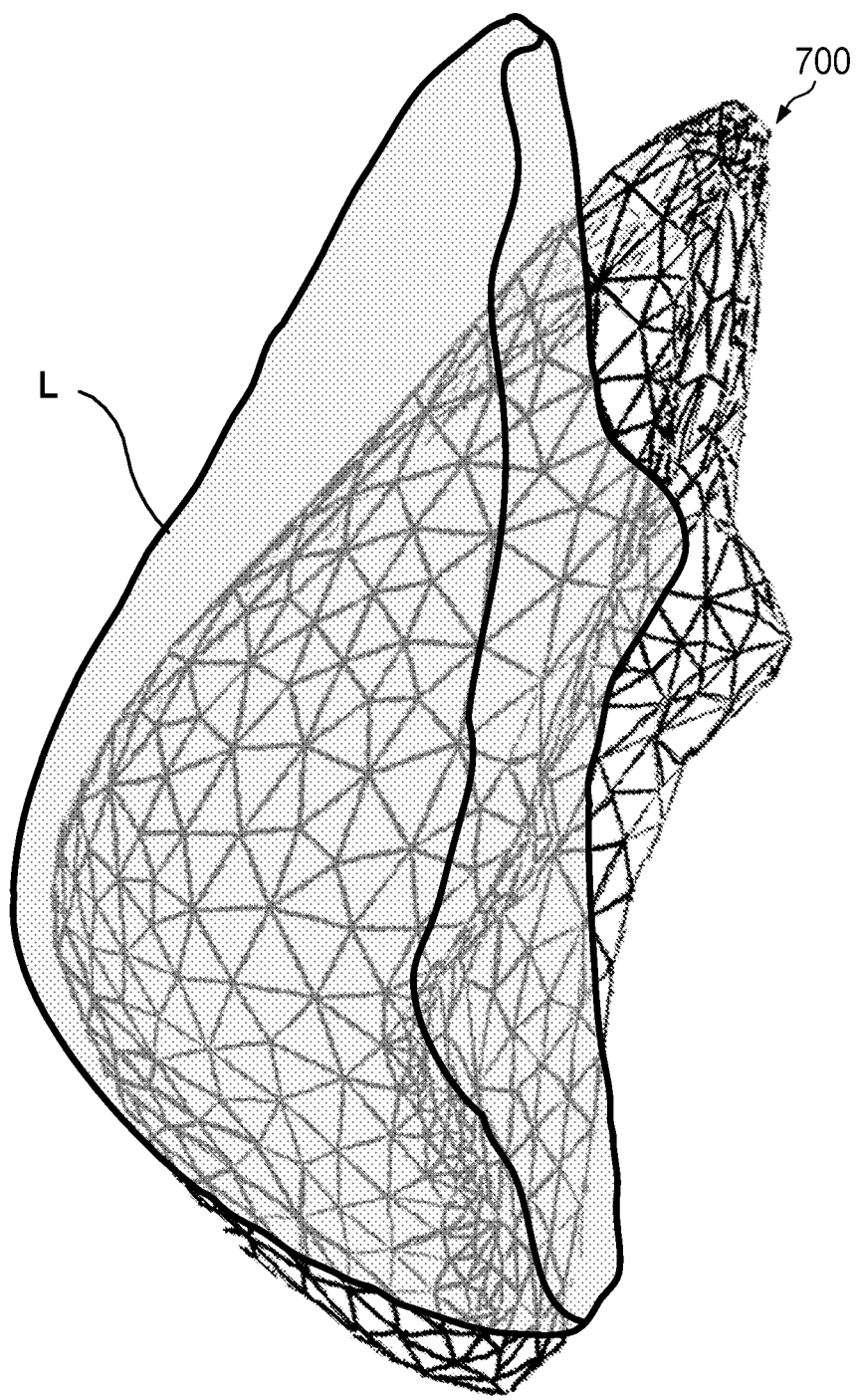
FIG. 8A depicts the relative orientations and positions of the model of FIG. 7 and the points of FIG. 6B representing the organ, according to aspects of the present disclosure.

At operation 510, the determined initial seed transformation may be applied. For example, the initial seed transformation may be used to bring the model 700 into the position shown in FIG. 8A. FIG. 8A depicts the relative orientations and positions of the model 700 and the liver L after application of the initial seed. As can be seen, even after application of the initial seed transformation, the positions and orientations of the actual liver L and the model 700 of the liver L may diverge so much that information from one source (i.e. actual observation versus preoperative or intraoperative observation that resulted in the model 700) cannot reliably be applied to the other source.

The iterative operation 512 may provide for usable registration between the liver L and the model 700. As illustrated in FIG. 5, the operation 512 includes a set of sub-operations that can be executed repeatedly in order to produce a satisfactory registration. The operation 512 may include an operation 514 of matching gathered data points to model points, and operation 516 of computing a motion based on the separation distances between matched points, and at operation 518 in which a transform is applied to the captured data points. These operations should bring the model 700 closer into alignment with the liver L. At operation 520, the convergence between the model 700 and liver L may be evaluated based on the two sets of three-dimensional points associated there with. More detailed information regarding the iterative operation 512 and the associated sub-operations is provided in Application No. PCT/US16/46633, filed Aug. 11, 2016, entitled "SYSTEMS AND METHODS OF REGISTRATION FOR IMAGE-GUIDED SURGERY," the disclosure of which is incorporated herein, in its entirety, by reference.

Figure 8B:
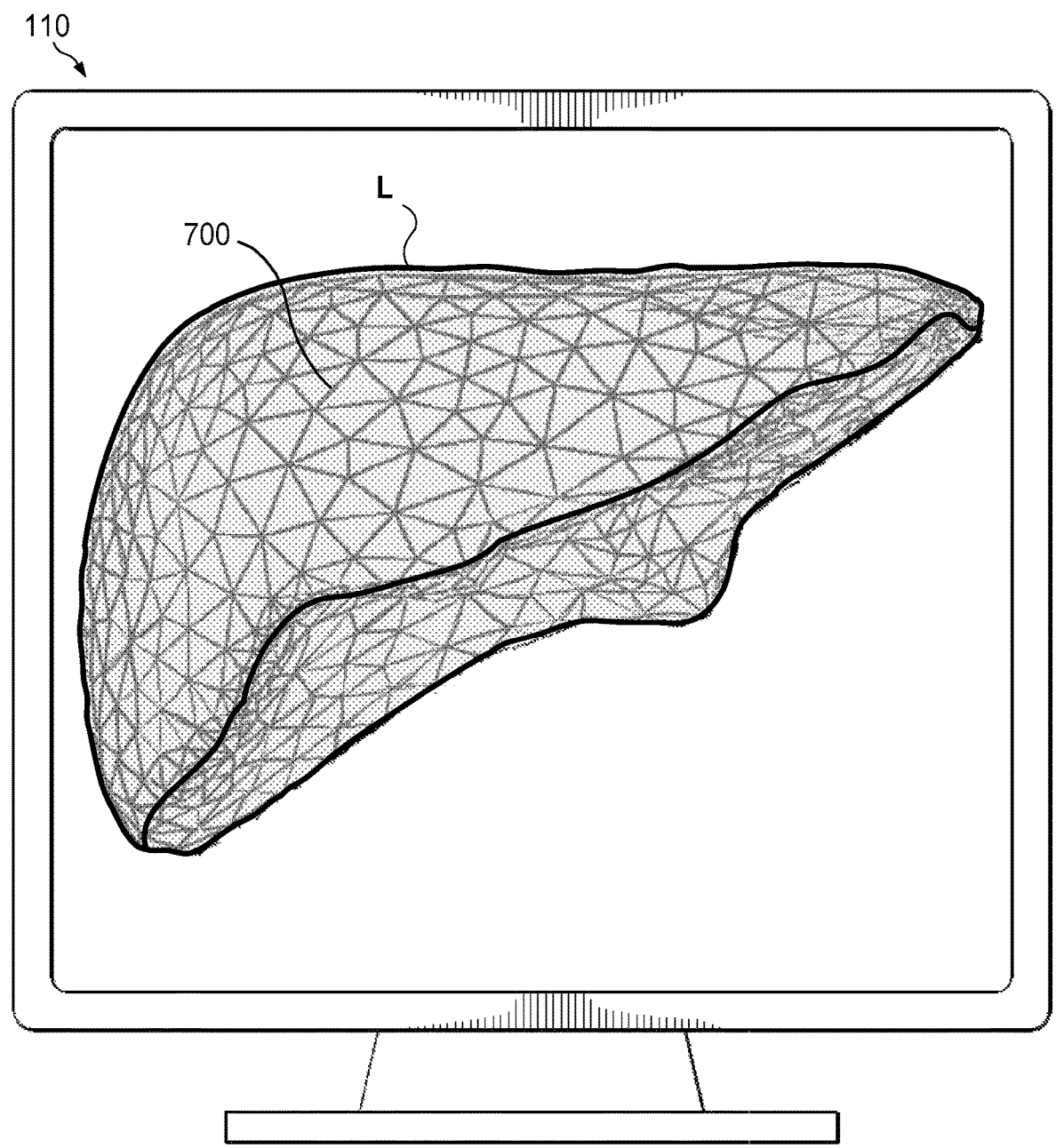
FIG. 8B depicts a registration between the model of FIG. 7 and the organ of FIG. 6B as rendered in a display, according to aspects of the present disclosure.

FIG. 8B depicts an exemplary satisfactory convergence between the model 700 and the actual liver L of the patient P as situated within the surgical environment, as displayed in a display system, like the display system 110 of FIG. 1. The control system 112 may cause the model and actual information, such as live video of the liver L, to be displayed simultaneously. Additionally, with the patient surgical space registered to the model space as described above, the current shape of the any instruments and the location of their distal end may be located and displayed concurrently with the rendering of the model 700. Alternatively, the model 700 may be superimposed over a live video feed.

The operator O may rely on information contained in the model 700 to perform a procedure on the liver L. For example, the model 700 may include an indication of a portion of the liver L to be surgically removed. The model 700 may be included in a user interface displayed on the display system 110 of FIG. 1A, along with a representation of the liver L, such as a live video feed. The feed may be obtained by the probe 278 or another system. The user interface may provide an indication to the operator O of the location and extent of the liver tissue to be surgically removed or to be observed for biopsy.

Furthermore, at operation 522, the control system 112 may determine a current location of any or all of the medical instruments 130A-C. At operation 524, one or more of the instruments 130A-C may be located relative to the model 700 because of the registration of the model 700 into a common reference frame with the surgical environment. For example, the instrument 130A may include an ablation probe or surgical scissors used to cut tissue from the liver L. The extent of tissue to be removed may be defined in the model 700, which having been brought into the same space as the liver L may be used by the control system 112 to confine operation of the ablation probe or surgical scissors to the defined volume in the model 700.

As noted, when the operator O causes a change in a surface used in the registration (i.e., the operator makes an incision in the surface from which points were collected to perform the initial seed transformation or registration) the control system 112 may indicate that the registration is unreliable or should be considered unreliable. In some embodiments, the control system 112 may determine that the current procedural step indicates to be made. The control system 112 may require a new registration as the subsequent procedural step in the workflow associated with the particular operation. In some embodiments, when a later registration replaces an earlier registration or an earlier registration is deemed replaceable by the control system 112 with a later registration, an alert may be provided to the clinician through a user interface to indicate that there is a change in registration, that a new registration is required, or that there is a superior registration available. In some embodiments, the control system 112 may require operator approval through the user interface before the superior registration is implemented. For example, when a superior registration is identified an alert may be rendered to the display system 110 along with a button or other user interface element by which the clinician can approve or disapprove to the new registration. The new registration will then be implemented or not depending on the clinician's decision.

As described above, the model and the localized instrument may be displayed to the operator O to aid in performing the medical procedure. Optionally, the operator, thus aided, may provide an operator input to control operation or movement of the instrument or arms 124A-D.

Although the systems and methods of this disclosure have been described for use in connection with liver surgery, the principles of the present disclosure may be applied in the performance of other procedures in which a modeled surface is to be registered to an actual surface. For example, a model of the kidney may be registered to a kidney, a model of the prostate may be registered to the prostate gland, etc. Because surfaces of such organs may be difficult to register to a pre-operative or intra-operative model, information regarding the position and pose of the imaging system 126 and information regarding the procedural setup of the operation may be particularly valuable in performing an initial seed transformation.

In some embodiments of the method 700 of FIG. 7, the registration process 712 may include an additional process in which weights for measured points are altered according to parameters or rules. The weights may be altered by adding a weight where no weight existed before or by changing the weigh associated with a given measured point. For example, in some embodiments more recently obtained points may be assigned a relatively higher weight. The relatively higher weight may be provided by incrementally decreasing the weights assigned to less recently obtained points as more time passes. More recently measured points may be more accurate due to movement of the patient, so by weighting the more recently measured points more than the less recently measured points the registration process 712 may be biased to reflect the most current information. The weights may be normalized weights or non-normalized.

In some embodiments, when a later registration replaces an earlier registration or an earlier registration is deemed replaceable by the control system 112 with a later registration, an alert may be provided to the clinician through a user interface to indicate that there is a change in registration or that there is a superior registration available. In some embodiments, the control system 112 may require clinician approval through the user interface before the superior registration is implemented. For example, when a superior registration is identified an alert may be rendered to the display system 110 along with a button or other user interface element by which the clinician can approve or disapprove to the new registration. The new registration will then be implemented or not depending on the clinician's decision.

One or more elements, including the methods 400 and 500, in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processor thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Embodiments to the present invention may facilitate the registration of a pre-operatively acquired set of modal points defining an anatomic model to a set of modal points intra-operatively acquired using a vision based approach. The sets of model points may be registered after an initial seed transformation is generated based on system information including extracted kinetic information and workflow information. This information may enable registration of tissue surfaces to facilitate image-guided and robotic surgeries to be performed on such tissue surfaces.

What is claimed is:

1. A non-transitory machine-readable medium comprising a plurality of machine-readable instructions which when executed by one or more processors associated with a medical system are adapted to cause the one or more processors to perform operations including:
    accessing a set of model points representing a model of a patient anatomy of interest;
    receiving a set of captured points acquired during visualization of a portion of the patient anatomy of interest with an imaging probe;
    obtaining system information from a medical system, wherein the system information comprises at least one of kinematic information from a robotic arm of the medical system or setup information associated with a medical procedure;
    generating an initial seed transformation based on the system information; and
    generating, by a control system processor of the medical system, a registration between the set of model points and the set of captured points using the initial seed transformation.

2. The non-transitory machine-readable medium of claim 1, wherein the plurality of machine-readable instructions, when executed by the one or more processors, are further adapted to cause the one or more processors to perform:
    detecting a change in the system information;
    updating the initial seed transformation based on the change in the system information; and
    generating, by the control system processor, a second registration between the set of model points and the set of captured points.

3. The non-transitory machine-readable medium of claim 1, wherein the plurality of machine-readable instructions, when executed by the one or more processors, are further adapted to cause the one or more processors to generate a surface model or a volumetric model from the set of model points.

4. The non-transitory machine-readable medium of claim 1, wherein the plurality of machine-readable instructions, when executed by the one or more processors, are further adapted to cause the one or more processors to display the set of model points as a surface model in a display, the surface model being oriented based on the registration.

5. A medical system comprising:
    a robotic manipulator arm;
    an imaging probe coupled to the robotic manipulator arm such that the imaging probe is movable in connection with the robotic manipulator arm; and
    a control system in communication with the robotic manipulator arm and the imaging probe, wherein the control system is configured to perform operations comprising:
        extracting system information, the system information including kinematic information from the robotic manipulator arm, setup information at least partially obtained from a kinematic chain of the robotic manipulator arm and an operator as an input, or a combination of the kinematic information and setup information associated with a medical procedure to be performed; and
        generating, by a control system processor, a registration between a set of model points of a model of a patient anatomy of interest and a set of intra-operatively collected captured points of a portion of the patient anatomy of interest, wherein the registration is based on the extracted system information.

6. The medical system of claim 5, wherein the setup information includes at least one of type of the medical procedure, location of anatomical target, point of entry, angle of entry, or a procedural step of the medical procedure.

7. The medical system of claim 5, wherein the control system is configured to perform operations including generating an initial seed transformation to be applied to the set of model points to translate the set of model points into a patient coordinate space, wherein the initial seed transformation is determined based on the system information.

8. The medical system of claim 7, wherein the control system is configured to perform operations including:
    detecting a change in the extracted system information;
    updating the initial seed transformation based on the change in the extracted system information; and
    generating, by the control system processor, a second registration between the set of model points and the set of captured points.

9. The medical system of claim 8, wherein the control system is configured to perform operations including:
    detecting a step in a workflow of the medical procedure; and
        overriding, based on the detection of the step, a default setting that updates the registration upon detection of the change.

10. The medical system of claim 5, wherein the set of model points includes pre-operative image data.

11. The medical system of claim 5, wherein the kinematic information from the robotic manipulator arm includes a plurality of servo positions and an angle formed by a shaft of the imaging probe with respect to a patient coordinate space.

12. The medical system of claim 5, wherein the robotic manipulator arm includes at least one of an encoder, an optical fiber, or a potentiometer for obtaining the kinematic information.

13. The medical system of claim 5, including a flexible catheter.

14. The medical system of claim 5, including a display system communicatively coupled to the control system and configured to present the set of model points as a surface model being oriented based on the registration.

15. The medical system of claim 14, wherein the display system is configured to present visual information from the imaging probe simultaneously with the surface model.

16. The medical system of claim 5, wherein the control system is configured to extract the kinematic information from the robotic manipulator arm of the medical system including identifying a roll of the vision imaging probe.

17. A medical system, comprising
    a robotic manipulator arm;
    an imaging probe coupled to the robotic manipulator arm such that the imaging probe is movable in connection with the robotic manipulator arm, wherein the imaging probe comprises a structured light three-dimensional scanner; and
    a control system in communication with the robotic manipulator arm and the imaging probe, wherein the control system is configured to perform operations comprising:
        extracting system information, the system information including kinematic information from the robotic manipulator arm, setup information, or a combination of the kinematic information and setup information associated with a medical procedure to be performed; and generating, by a control system processor, a registration between a set of model points of a model of a patient anatomy of interest and a set of intra-operatively collected captured points of a portion of the patient anatomy of interest, wherein the registration is based on the extracted system information.

18. The medical system of claim 17, wherein the structured light three-dimensional scanner is disposed at a distal end of a catheter.

\* \* \* \* \*